US012633906B2

(12) United States Patent
Aithal et al.

(10) Patent No.: US 12,633,906 B2
(45) Date of Patent: May 19, 2026

(54) ECG INTERFERENCE SUPPRESSION

(71) Applicant: Texas Instruments Incorporated, Dallas, TX (US)

(72) Inventors: Sachin Aithal, Bangalore (IN); Anand H Udupa, Bangalore (IN); Raja Reddy Patukuri, Bengaluru (IN); Sandeep Oswal, Bangalore (IN); Aatish Chandak, Bangalore (IN); Vignesh Subramanya, Bangalore (IN); Aravind Miriyala, Bangalore (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 245 days.

(21) Appl. No.: 18/589,715

(22) Filed: Feb. 28, 2024

(65) Prior Publication Data

US 2024/0313751 A1     Sep. 19, 2024

(30) Foreign Application Priority Data

Mar. 16, 2023     (IN) ............................. 202341017914

(51) Int. Cl.
| | |
|---|---|
| *H03D 1/04* | (2006.01) |
| *A61B 5/00* | (2006.01) |
| *A61B 5/349* | (2021.01) |
| *H03K 5/1252* | (2006.01) |
| *H03M 1/12* | (2006.01) |

(52) U.S. Cl.
CPC ........... *H03K 5/1252* (2013.01); *A61B 5/349* (2021.01); *A61B 5/7217* (2013.01); *H03M 1/12* (2013.01)

(58) Field of Classification Search
CPC .... H03K 5/1252; A61B 5/349; A61B 5/7217; H03M 1/12
USPC ................................. 375/346, 316, 295, 219
See application file for complete search history.

(56) References Cited

U.S. PATENT DOCUMENTS

2011/0319777 A1* 12/2011 Mehrotra ............. A61B 5/0006
600/509

* cited by examiner

*Primary Examiner* — Zewdu A Kassa
(74) *Attorney, Agent, or Firm* — Xianghui Huang; Frank D. Cimino

(57) ABSTRACT

A circuit includes an interference frequency tracking circuit, a PLI synthesizer circuit, and a summing circuit. The interference frequency tracking circuit is configured to track a frequency of an interference signal derived from a target signal, and provide a frequency selection value representing the frequency of the interference signal. The PLI synthesizer circuit is configured to generate, based on the frequency selection value, a correction signal at the frequency of the interference signal, adjust a phase of the correction signal to match a phase of the interference signal in the target signal, and adjust an amplitude of the correction signal to match an amplitude of the interference signal in the target signal. The summing circuit is configured to subtract the correction signal from the target signal.

20 Claims, 14 Drawing Sheets

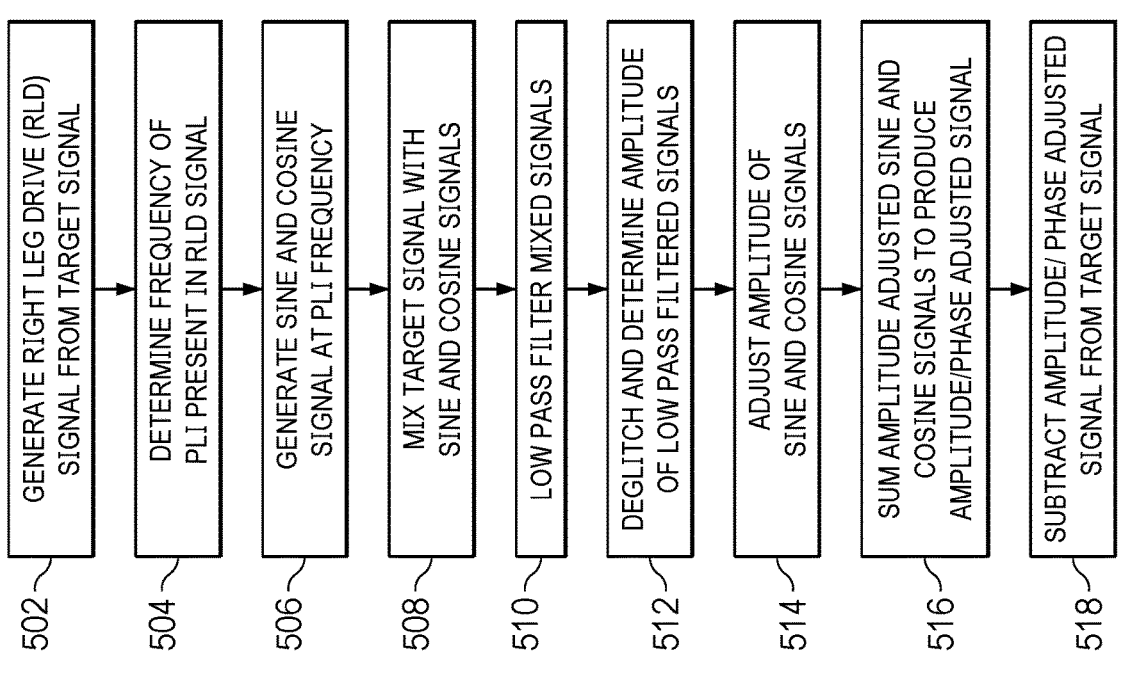

502 — GENERATE RIGHT LEG DRIVE (RLD) SIGNAL FROM TARGET SIGNAL

504 — DETERMINE FREQUENCY OF PLI PRESENT IN RLD SIGNAL

506 — GENERATE SINE AND COSINE SIGNAL AT PLI FREQUENCY

508 — MIX TARGET SIGNAL WITH SINE AND COSINE SIGNALS

510 — LOW PASS FILTER MIXED SIGNALS

512 — DEGLITCH AND DETERMINE AMPLITUDE OF LOW PASS FILTERED SIGNALS

514 — ADJUST AMPLITUDE OF SINE AND COSINE SIGNALS

516 — SUM AMPLITUDE ADJUSTED SINE AND COSINE SIGNALS TO PRODUCE AMPLITUDE/PHASE ADJUSTED SIGNAL

518 — SUBTRACT AMPLITUDE/ PHASE ADJUSTED SIGNAL FROM TARGET SIGNAL

FIG. 5

ECG INTERFERENCE SUPPRESSION

CROSS-REFERENCE TO RELATED APPLICATIONS

This application claims priority to Indian Provisional Application No. 202341017914, filed Mar. 16, 2023, entitled "RLD Based Tracking and Adaptive Filtering of ECG Signals to Remove Powerline Interference in a Multichannel AFE," which is hereby incorporated by reference.

BACKGROUND

Electrocardiography (ECG or EKG) is a transthoracic (across the thorax or chest) interpretation of the electrical activity of the heart over a period of time, as detected by electrodes attached to the outer surface of the skin and recorded by a device external to the body. The recording of cardiac electrical activity produced by this noninvasive procedure is called an electrocardiogram (also ECG or EKG). An ECG is used to measure the rate and regularity of heartbeats as well as the size and position of the heart chambers, the presence of any damage to the heart, and the effects of drugs or devices used to regulate the heart, such as a pacemaker.

SUMMARY

In one example, a circuit includes an interference frequency tracking circuit, a power line interference (PLI) synthesizer circuit, and a summing circuit. The interference frequency tracking circuit includes an analog-to-digital converter (ADC), a bandpass filter circuit, a cyclic event detector, an averaging circuit, and a frequency selection circuit. The ADC has an output. The ADC is configured to digitize an interference signal extracted from a target signal. The bandpass filter circuit has an input coupled to the output of the ADC, and an output. The bandpass filter is configured to pass a frequency range of the interference signal. The cyclic event detector has an input coupled to the output of the bandpass filter circuit, and an output. The cyclic event detector is configured to identify a cyclic event of the interference signal. The averaging circuit has an input coupled to the output of the cyclic event detector, and an output. The averaging circuit is configured to provide an average time value representing an average time between events detected by the cyclic event detector. The frequency selection circuit has an input coupled to the output of the averaging circuit, and an output. The frequency selection circuit is configured to provide a frequency selection value representing the frequency of the interference signal based on the average time. The PLI synthesizer circuit has an input coupled to the output of the frequency selection circuit, and an output. The PLI synthesizer circuit is configured to generate a correction signal based on the frequency selection value. The summing circuit has an input coupled to the output of the PLI synthesizer circuit. The summing circuit is configured to subtract the correction signal from the target signal.

In another example, a circuit includes an interference frequency tracking circuit, a PLI synthesizer circuit, and a summing circuit. The interference frequency tracking circuit has an output, and is configured to track a frequency of an interference signal derived from a target signal, and provide a frequency selection value representing the frequency of the interference signal. The PLI synthesizer circuit has an input coupled to the output of the interference frequency tracking circuit, and an output. The PLI synthesizer circuit is configured to generate, based on the frequency selection value, a correction signal at the frequency of the interference signal, adjust a phase of the correction signal to match a phase of the interference signal in the target signal, and adjust an amplitude of the correction signal to match an amplitude of the interference signal in the target signal. The summing circuit has a first input coupled to the output of the PLI synthesizer circuit. The summing circuit is configured to subtract the correction signal from the target signal.

In a further example, an electrocardiogram (ECG) system includes an interference suppression circuit. The interference suppression circuit has an ECG signal input, a right leg drive (RLD) signal input coupled to an RLD terminal, and an ECG signal output. The interference suppression circuit includes an interference frequency tracking circuit, a PLI synthesizer circuit, and summing circuit. The interference frequency tracking circuit has an RLD input coupled to an RLD terminal that provides an RLD signal, and a frequency output. The interference frequency tracking circuit is configured to track a frequency of a PLI signal present in the RLD signal, and provide, at the frequency output, a frequency selection value representing the frequency of the PLI signal. The PLI synthesizer circuit has an input coupled to the frequency output of the interference frequency tracking circuit, and a synthesizer output. The PLI synthesizer circuit is configured to provide a correction signal based on the frequency selection value. The summing circuit has a first input coupled to the synthesizer output of the PLI synthesizer circuit, a second input coupled to the ECG signal input. The summing circuit is configured to subtract the correction signal from the ECG signal.

BRIEF DESCRIPTION OF THE DRAWINGS

FIG. 5 is a flow diagram for an example method for suppressing power line interference.

DETAILED DESCRIPTION

Figure 1:
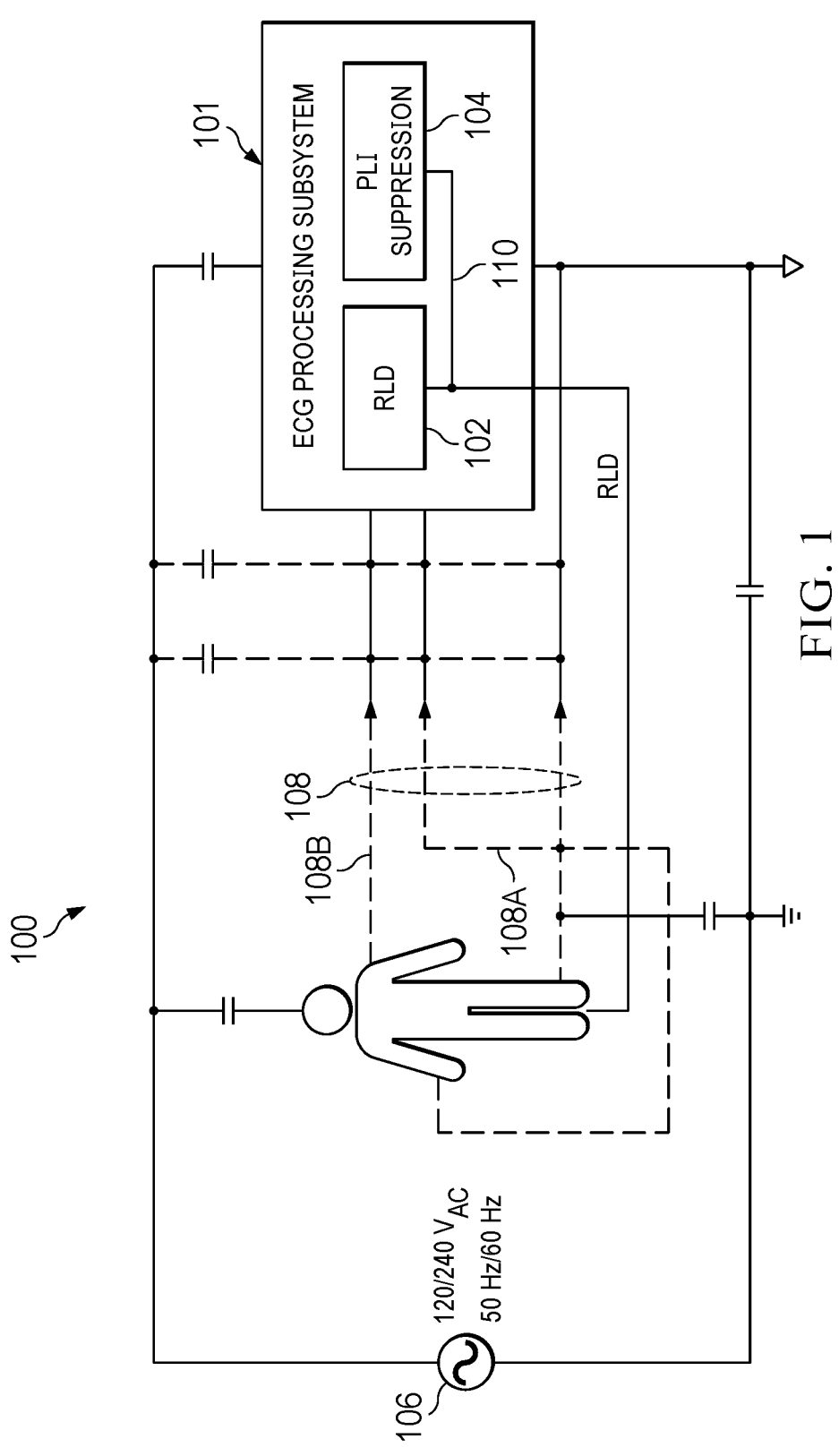
FIG. 1 is a block diagram of an example electrocardiography (ECG) system.

FIG. 1 is a block diagram of an example electrocardiography (ECG) system 100. The ECG system 100 includes an ECG processing subsystem 101 and conductive leads 108. The conductive leads 108 include electrodes that can be attached to a subject whose cardiac activity is to be monitored, and the conductive leads 108 conduct electrical signals acquired from the subject to the ECG processing subsystem 101. The ECG processing subsystem 101 processes the electrical signals to provide a display or record of the electrical signals for interpretation.

Figure 2:
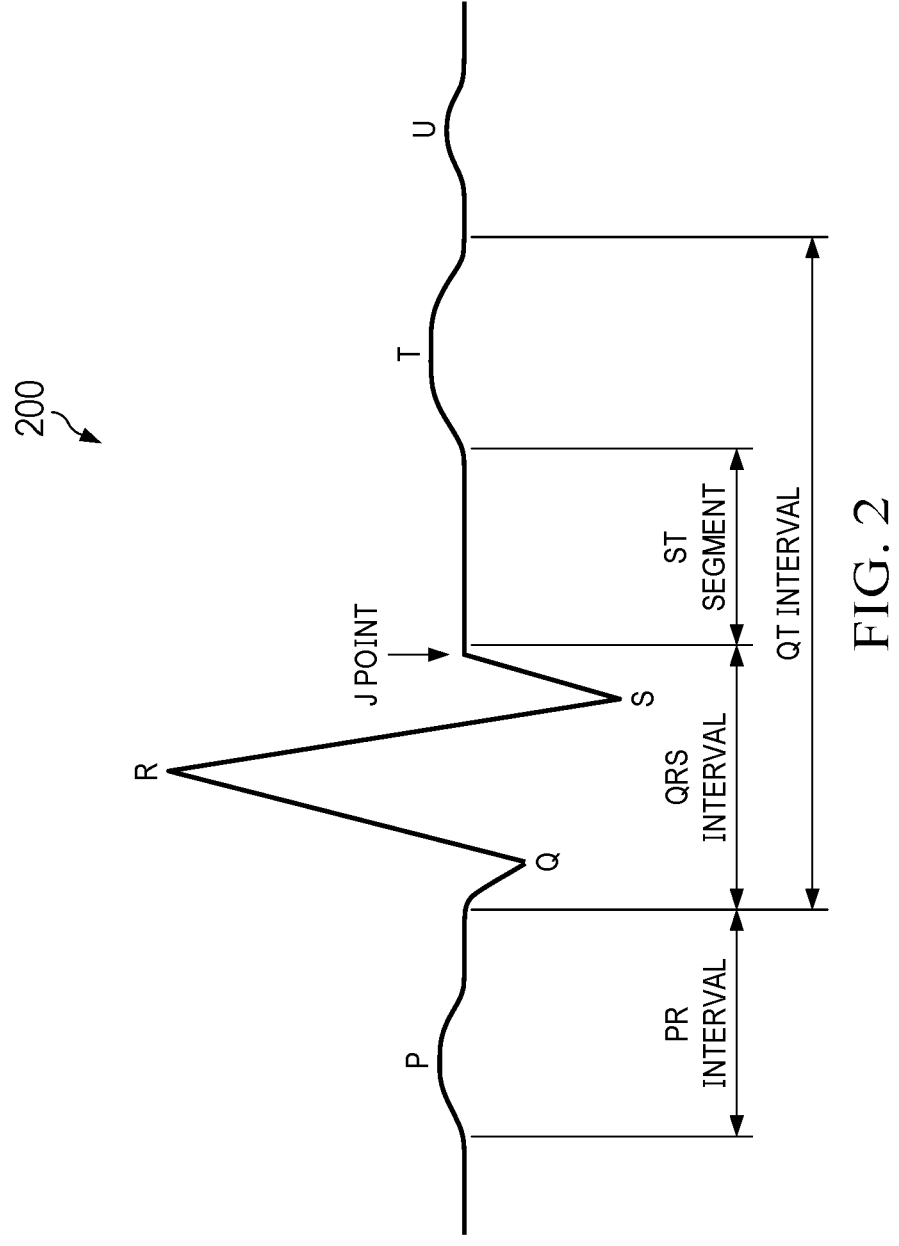
FIG. 2 is a graph of an example ECG waveform.

FIG. 2 is a graph of an example ECG signal 200 in the ECG system 100. The ECG signal 200 represents the electrical activity of the heart and has an amplitude of about 1 millivolt (mV). The ECG signal 200 is partitioned into three main waves—a P wave, QRS complex, and a T wave. Each of these waves represent a specific operation (either depolarization or repolarization) of atria and ventricles of the heart. Clinical interpretation of an ECG signal depends on the shape and length (or duration) of these waves.

Figure 3:
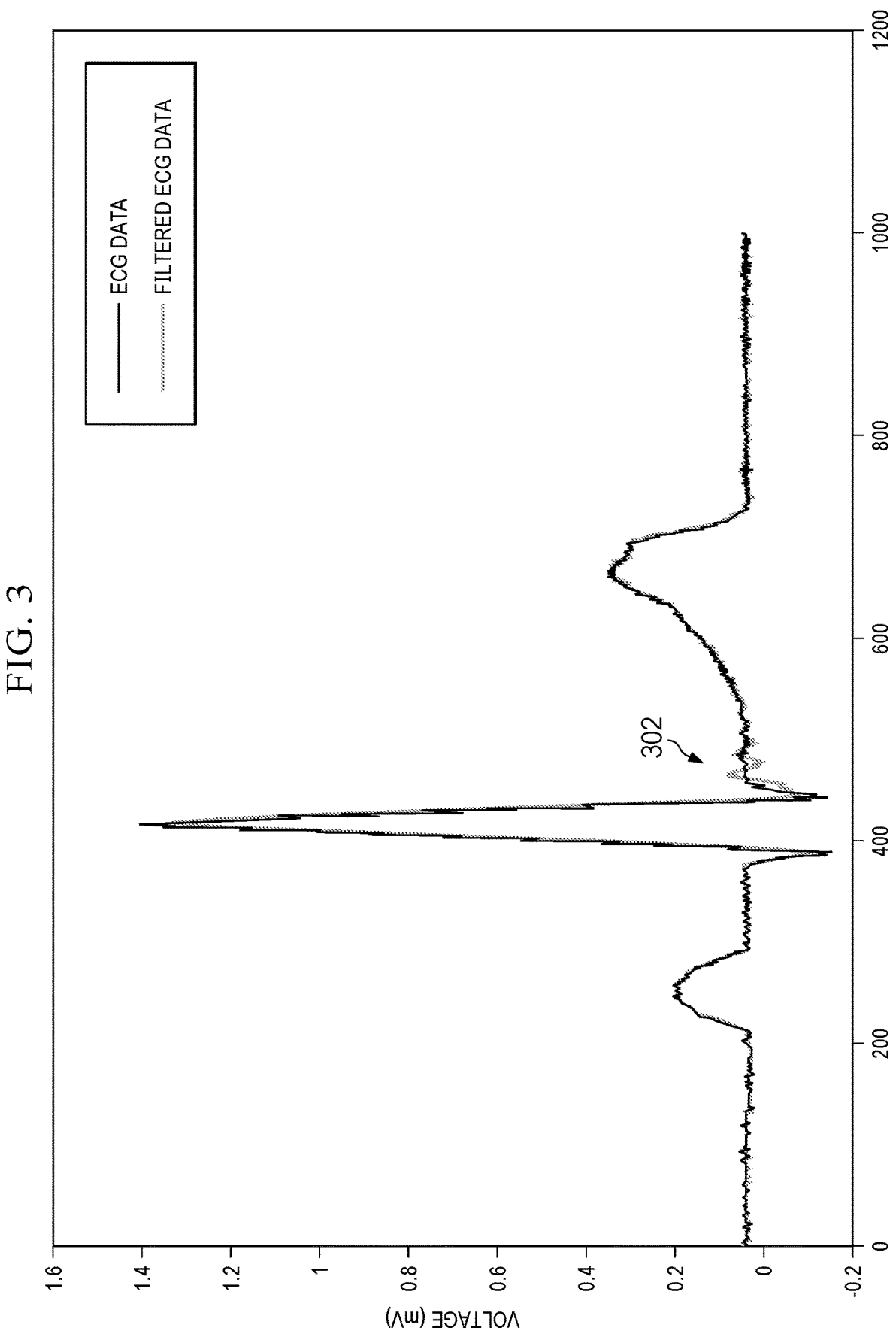
FIG. 3 is a graph of an example ECG waveform showing ringing produced by a notch filter applied to reduce power line interference.

Accurate interpretation of ECG signals may be facilitated by suppressing undesirable interfering signals, such as powerline interference (PLI). PLI is 50 or 60 Hertz (Hz) signal (and harmonics thereof) that is capacitively, inductively, or otherwise coupled from the AC power lines onto the ECG signals. As shown in FIG. 1 a powerline interference source 106 is present in the operating environment of the ECG system 100, and 50 Hz or 60 Hz, and harmonics thereof, may be coupled to the subject, the conductive leads 108, and/or the ECG processing subsystem 101, and corrupt the ECG signals. The frequency and amplitude of PLI can vary with time and/or load. To mitigate PLI, some ECG systems apply notch filtering in a frequency band including the range of the PLI frequencies. However, the notch filter distorts the ECG signals, which can impede ECG interpretation. FIG. 3 is a graph of an example ECG waveform 300 sampled at 1 kilo-sample-per-second (KSPS) that is passed through a $2^{nd}$ order 50 Hz infinite impulse response (IIR) notch filter with a notch width of about 0.31 Hz around 50 Hz and having >30 dB attenuation. The notch filter causes substantial ringing 302 on the ST segment of the filtered ECG signal due to the impulsive nature of QRS complex. Such artifacts make notch filtering undesirable. Notch filtering is also of limited usefulness in the presence of PLI amplitude variation and pacemaker pulses.

Returning to FIG. 1, the ECG processing subsystem 101 includes a right leg drive (RLD) circuit 102, and a PLI suppression circuit 104. The RLD circuit 102 reduces PLI by extracting a common-mode signal from the ECG signal received via the conductive leads 108, and driving the common-mode signal out of phase as an RLD signal (shown as RLD in FIG. 1). The common-mode signal includes the PLI. The RLD circuit 102 may extract the common mode signal by averaging signals provided by multiple of the conductive leads 108. Some implementations of the RLD circuit 102 may extract the common mode signal from the ECG signal by, for example, using a pair of resistors to sum (average) ECG signals received via the right and left arm conductive leads 108A and 108B. The summation cancels differential signal, leaving the common mode signal, which includes PLI and other common mode signals. The RLD circuit 102 may drive the RLD signal onto a conductor coupled to the subject (e.g., the right leg of the subject). For example, the RLD circuit 102 may include an inverting amplifier that drives the common mode signal extracted by the resistive summation as the signal RLD shown in FIG. 1.

The RLD circuit 102 may significantly reduce the PLI on the ECG signal (e.g., from 100s of mV to 10s of mV). However, the RLD circuit 102 does not eliminate PLI.

The PLI suppression circuit 104 has an input (an RLD signal input) coupled to an RLD terminal 110 and an output of the RLD circuit 102. The PLI suppression circuit 104 receives the RLD signal generated by the RLD circuit 102, digitizes the RLD signal, and tracks the frequency of the PLI in the RLD signal. Having determined the frequency of the PLI, the PLI suppression circuit 104 tracks the phase and amplitude of the PLI in the ECG signal, and generates a correction signal having the frequency, phase, and amplitude of the PLI. The PLI suppression circuit 104 subtracts the correction signal from the ECG signal to suppress PLI. Accordingly, the PLI suppression circuit 104 effectively suppresses PLI across variation in PLI frequency and amplitude.

Figure 4:
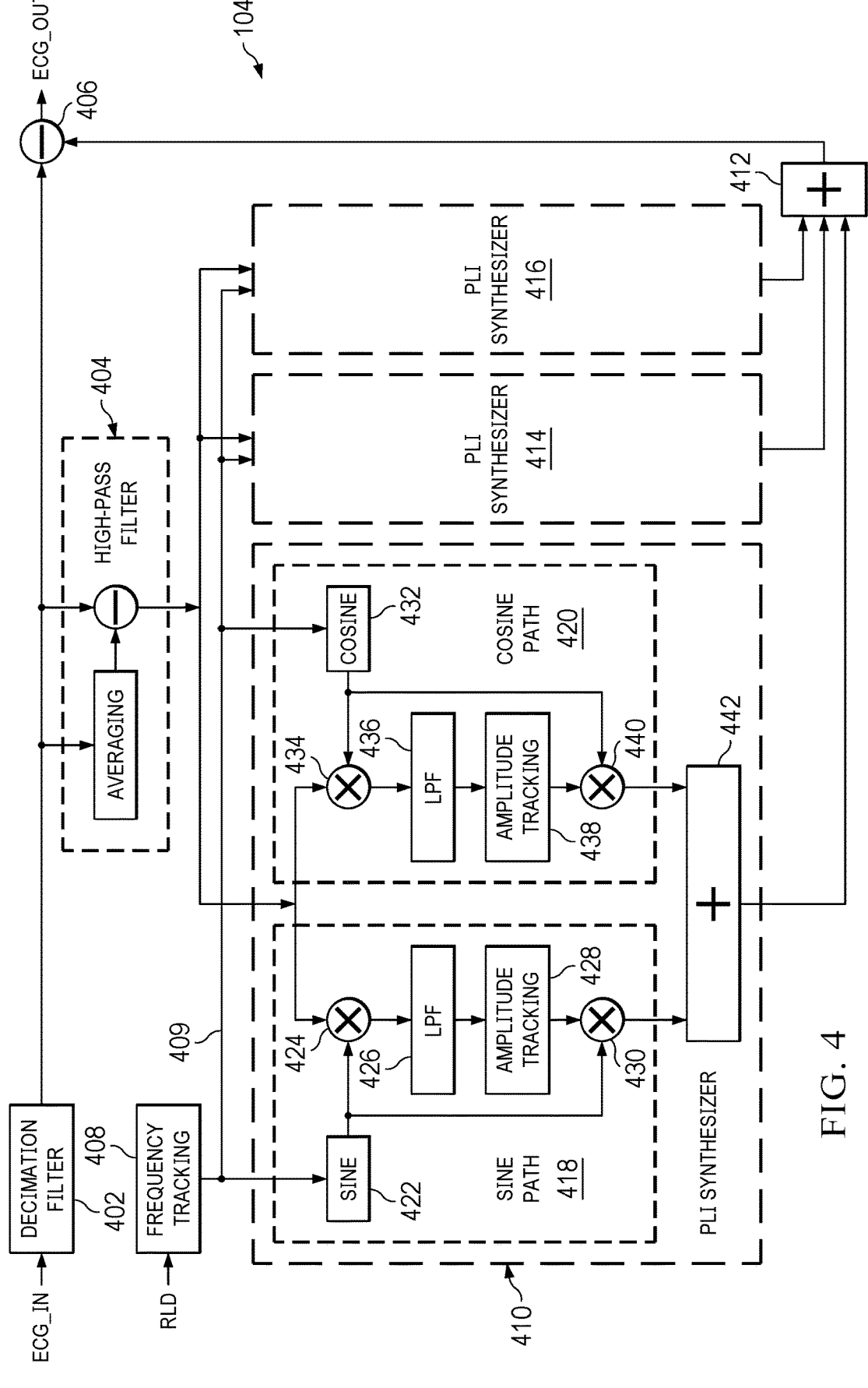
FIG. 4 is a block diagram of an example power line interference suppression circuit.

FIG. 4 is a block diagram of an example PLI suppression circuit 104. The PLI suppression circuit 104 includes a decimation filter 402, a high-pass filter 404, a summing circuit 406, a frequency tracking circuit 408 (also referred to as an interference frequency tracking circuit), PLI synthesizer circuits 410, 414, and 416, and a summing circuit 412. Also shown in FIG. 4 is an ECG_IN signal and an RLD signal received into the PLI suppression circuit 104 and an ECG_OUT signal provided by the PLI suppression circuit 104. The signal ECG_IN may be an amplified and digitized version of an electrical signal detected at one or more of the electrodes provided with the conductive leads 108. Circuitry for amplifying and digitizing the ECG signals received via the conductive leads 108 has been omitted from this description in the interest of clarity. The signal RLD is received from the RLD circuit 102 as shown in FIG. 1. The signal ECG_OUT is, in large part, the signal ECG_IN filtered by the PLI suppression circuit 104 to attenuate PLI. The signal ECG_OUT may be provided to processing, recording, and/or display circuits of the ECG system 100 (not shown).

The decimation filter 402 receives the digitized ECG signal, and decimates the ECG signal (e.g., decimates the ECG signal to a rate of 1000 samples-per-second). The high-pass filter 404 is coupled to the decimation filter 402. The high-pass filter 404 calculates a block average of a relatively large number of samples (e.g., 1024 samples) provided by the decimation filter 402, and subtracts the average from the ECG samples provided by the decimation filter 402. Accordingly, the high-pass filter 404 removes DC from the ECG signal provided to the PLI synthesizer circuits 410, 414, and 416, and passes PLI signal frequencies. The high-pass filter 404 provides the high-pass filtered ECG signal to the PLI synthesizer circuits 410, 414, and 416.

The frequency tracking circuit 408 tracks the frequency of the PLI present in the RLD signal. Operation of the frequency tracking circuit 408 will be described with reference to FIG. 6. The frequency tracking circuit 408 generates a frequency selection value 409 that represents the frequency of the PLI, and provides the frequency selection value 409 to the PLI synthesizer circuits 410, 414, and 416. The PLI synthesizer circuits 410, 414, and 416 generate correction signals having a frequency based on the frequency selection value 409, and phase and amplitude determined by mixing the PLI frequency and the ECG signal. The PLI synthesizer circuit 410 generates a correction signal at the fundamental frequency of the PLI. The PLI synthesizer circuit 414 generates a correction signal at the second harmonic of the PLI. The PLI synthesizer circuit 416 generates a correction signal at the third harmonic of the PLI. The summing circuit 412 has inputs coupled to the outputs of the PLI synthesizer circuits 410, 414, and 416. The summing circuit 412 sums the correction signals generated by the PLI synthesizer circuits 410, 414, and 416 to generate a composite correction signal. The summing circuit 406 has an input coupled to an output of the summing circuit 412 and an input coupled to the output of the decimation filter 402. The summing circuit 406 subtracts the composite correction signal provided by the summing circuit 412 from the ECG signal provided by the decimation filter 402 to produce an ECG output signal having substantially reduced PLI. Some examples of the PLI suppression circuit 104 may include more or less PLI synthesizer circuits than are shown in FIG. 4 to generate correction signals at desired harmonics of the PLI.

In the PLI synthesizer circuits 410, 414, and 416, PLI amplitude information is extracted from the ECG signal by: I-Q demodulating the ECG signal with the PLI frequency signal (a signal having the same frequency as the PLI); followed by (b) low pass filtering; and then (c) re-modulating the low-pass output signal with the PLI frequency signal to generate an amplitude matched and frequency matched correction signal for a harmonic or the fundamental of the PLI. An amplitude tracking circuit is provided after the low pass filter to null impulses on the low-pass filter output signal caused by the QRS complex of the ECG signal or any other pulse interferers like pacemaker pulses. The phase of the PLI is automatically tracked by use of I-Q based demodulation and remodulation.

The PLI synthesizer circuit 410 includes a PLI sine estimation circuit 418, a PLI cosine estimation circuit 420, and a summing circuit 442. The PLI sine estimation circuit 418 includes a sine generator circuit 422, a multiplier 424, a low-pass filter circuit 426, an amplitude tracking circuit 428, and a multiplier 430. The sine generator circuit 422 generates sine samples at a frequency (referred to as a sine frequency) specified by the frequency selection value 409. For example, the sine generator circuit 422 may access a table of sine samples with indexing selected to provide a sine at the frequency represented by the frequency selection value 409. An output of the sine generator circuit 422 is coupled to a first input of the multiplier 424 and a first input of the multiplier 430. A second input of the multiplier 424 is coupled to the output of the high-pass filter 404 for receipt of the high-pass filtered ECG signal. The multiplier 424 multiplies (mixes) the ECG signal received from the high-pass filter 404 and the PLI frequency signal received from the sine generator circuit 422.

An output of the multiplier 424 is coupled to an input of the low-pass filter circuit 426. The low-pass filter circuit 426 can be implemented as a finite impulse response filter that attenuates the PLI frequency and its harmonics, and passes DC (which corresponds to the amplitude of the PLI). An output of the low-pass filter circuit 426 is coupled to an input of the amplitude tracking circuit 428. The amplitude tracking circuit 428 receives the low-pass output signal provided by the low-pass filter circuit 426, and provides an amplitude signal that tracks the amplitude of the PLI. The amplitude tracking circuit 428 tracks the amplitude of the PLI by identifying and ignoring ECG components and other transient signals that are not PLI related. Operation of the amplitude tracking circuit 428 will be described with reference to FIG. 8.

An output of the amplitude tracking circuit 428 is coupled to a second input of the multiplier 430. The multiplier 430 multiplies the amplitude signal received from the amplitude tracking circuit 428 and the PLI frequency sine signal received from the sine generator circuit 422. The multiplier 430 provides the amplitude adjusted PLI frequency sine signal to the summing circuit 442. An output of the multiplier 430 is coupled to a first input of the summing circuit 442.

The PLI cosine estimation circuit 420 includes a cosine generator circuit 432, a multiplier 434, a low-pass filter circuit 436, an amplitude tracking circuit 438, and a multiplier 440. The cosine generator circuit 432 generates cosine samples for a cosine signal having a frequency specified by the frequency selection value 409. Using the cosine samples, the multiplier 434, the low-pass filter circuit 436, the amplitude tracking circuit 438 and the multiplier 440 operate in the same way as the multiplier 424, the low-pass filter circuit 426, the amplitude tracking circuit 428, and the multiplier 440. The multiplier 440 provides the amplitude adjusted PLI frequency cosine signal to the summing circuit 442. An output of the multiplier 440 is coupled to a second input of the summing circuit 442. The summing circuit 442 sums the amplitude adjusted sine and cosine signals (the output signals) received from the PLI sine estimation circuit 418 and the PLI cosine estimation circuit 420 to produce a correction signal that matches the phase and amplitude of the PLI in the ECG signal. In the PLI synthesizer circuit 410, the correction signal is provided at a fundamental frequency of the PLI. In some examples of the 104, the difference between the actual frequency of the PLI and the frequency of the correction signal may be no more than about 5-10 milli-Hertz, and the difference between the actual amplitude of the PLI and the amplitude of the correction signal may be no more than about 10-30 millivolts.

The PLI synthesizer circuits 414 and the 416 include circuitry similar (e.g., PLI sine and cosine estimation circuits, and summation circuits) to that of the PLI synthesizer circuit 410. However, in the PLI synthesizer circuit 414, the sine and cosine signal generated are twice the frequency of the those generated by the PLI synthesizer circuit 410. In the PLI synthesizer circuit 416, the sine and cosine signal generated are three times the frequency of the those generated by the PLI synthesizer circuit 410.

FIG. 5 is a flow diagram for an example method 500 for suppressing PLI. Though depicted sequentially as a matter of convenience, at least some of the actions shown can be performed in a different order and/or performed in parallel. Additionally, some implementations may perform only some of the actions shown. Operations of the method 500 may be performed by the ECG processing subsystem 101.

In block 502, the RLD circuit 102 generates an RLD signal by extracting a common mode signal from an ECG signal.

In block 504, the PLI suppression circuit 104 determines and tracks the frequency of the PLI present in the RLD signal. For example, the frequency tracking circuit 408 tracks (determines across changes in frequency) the frequency of the PLI present in the RLD signal, and provides a frequency selection value representing the frequency of the PLI.

In block 506, the PLI suppression circuit 104 generates sine and cosine signals at the frequency of the PLI present in the RLD signal. For example, the sine generator circuit 422 and the cosine generator circuit 432 of the PLI synthesizer circuit 410 respectively generate sine and cosine signals at the frequency represented by the frequency selection value.

In block 508, the multiplier 424 of the PLI synthesizer circuit 410 mixes the sine and cosine signals with the high pass filtered ECG signal.

In block 510, the low-pass filter circuit 426 of the PLI synthesizer circuit 410 low pass filters the mixed signal generated in block 508. The low pass filtering can greatly attenuate the signal at and above the PLI frequency, and pass DC that represents the amplitude of the PLI.

In block 512, the amplitude tracking circuit 428 of the PLI synthesizer circuit 410 identifies and removes transients (deglitches) in the low pass filtered signal generated in block 510, and determines and tracks the amplitude of the low pass filtered signal. Sine and cosine amplitude values are generated by the amplitude determination and tracking.

In block 514, the multiplier 430 of the PLI synthesizer circuit 410 applies the amplitude values generated in block 512 to adjust the amplitude of the sine and cosine signals generated in block 506.

In block 516, the summing circuit 442 of the PLI synthesizer circuit 410 sums the amplitude adjusted sine and cosine signals generated in block 512 to produce an amplitude and phase adjusted correction signal at the PLI frequency.

In block 518, the summing circuit 406 of the PLI suppression circuit 104 subtracts the correction signal from the target signal (the ECG signal) to suppress PLI in the target signal.

Figure 6:
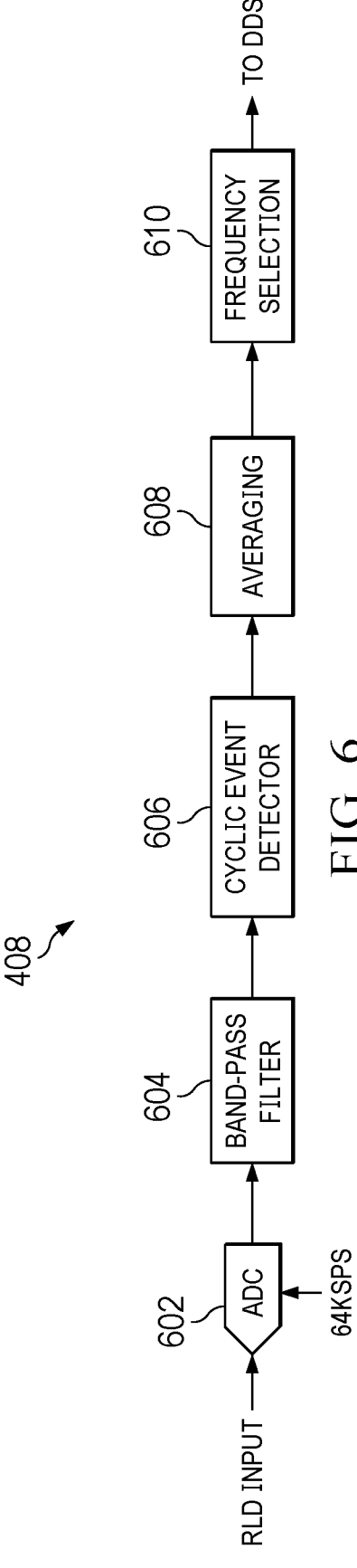
FIG. 6 Is a block diagram of an example frequency tracking circuit suitable for use in the power line interference suppression circuit of FIG. 4.

FIG. 6 is a block diagram of an example frequency tracking circuit 408. The frequency tracking circuit 408 includes an analog-to-digital converter 602, a band-pass filter 604, a cyclic event detector 606, an averaging circuit 608, and a frequency selection circuit 610. An analog signal input of the analog-to-digital converter 602 is coupled to the output of the RLD circuit 102 for receipt of the RLD signal. The analog-to-digital converter 602 digitizes the RLD signal. A digital output of the analog-to-digital converter 602 is coupled to an input of the band-pass filter 604. The band-pass filter 604 passes signal in a pass band selected to include the PLI signal within the RLD signal, and attenuates frequencies above or below the pass band. In some examples, the band-pass filter 604 may be an 8th order IIR band-pass filter having a pass band of about 45 Hz to 65 Hz.

An output of the band-pass filter 604 is coupled to an input of the cyclic event detector 606. The cyclic event detector 606 detects a cyclic event in the PLI signal, such as a peak or a zero crossing, and times from one event to the next event. An output of the cyclic event detector 606 is coupled to an input of the averaging circuit 608. The averaging circuit 608 averages a selected number of inter-event time values received from the cyclic event detector 606. Averaging is one example of filtering that the averaging circuit 608 can apply to the inter-event time values to improve the accuracy of the PLI frequency estimation. Some examples of the averaging circuit 608 may apply different filtering, e.g., different low pass filtering. Accordingly, the averaging circuit 608 may also be referred to as a filtering circuit. Inter-event time is the time between cyclic events (e.g., time between peaks or time between zero crossings). For example, the averaging circuit 608 may average 8 time values. In another example, the average is a moving average that changes over time as the PLI signal changes.

An output of the averaging circuit 608 is coupled to an input of the frequency selection circuit 610. The averaging circuit 608 provides the average inter-event time values to the frequency selection circuit 610, and the frequency selection circuit 610 generates a frequency selection value based on the inter-event time value. For example, the frequency selection circuit 610 may include a lookup table that provides frequency selection values based on inter-event time values. The frequency selector value represents the frequency of the PLI signal. As the frequency of the PLI signal changes over time, the inter-event time values and the frequency selection values change to track the frequency of the PLI signal. The PLI synthesizer circuit 410 applies the frequency selection value to generate sine and cosine signals that track the frequency of the PLI signal.

Figure 7:
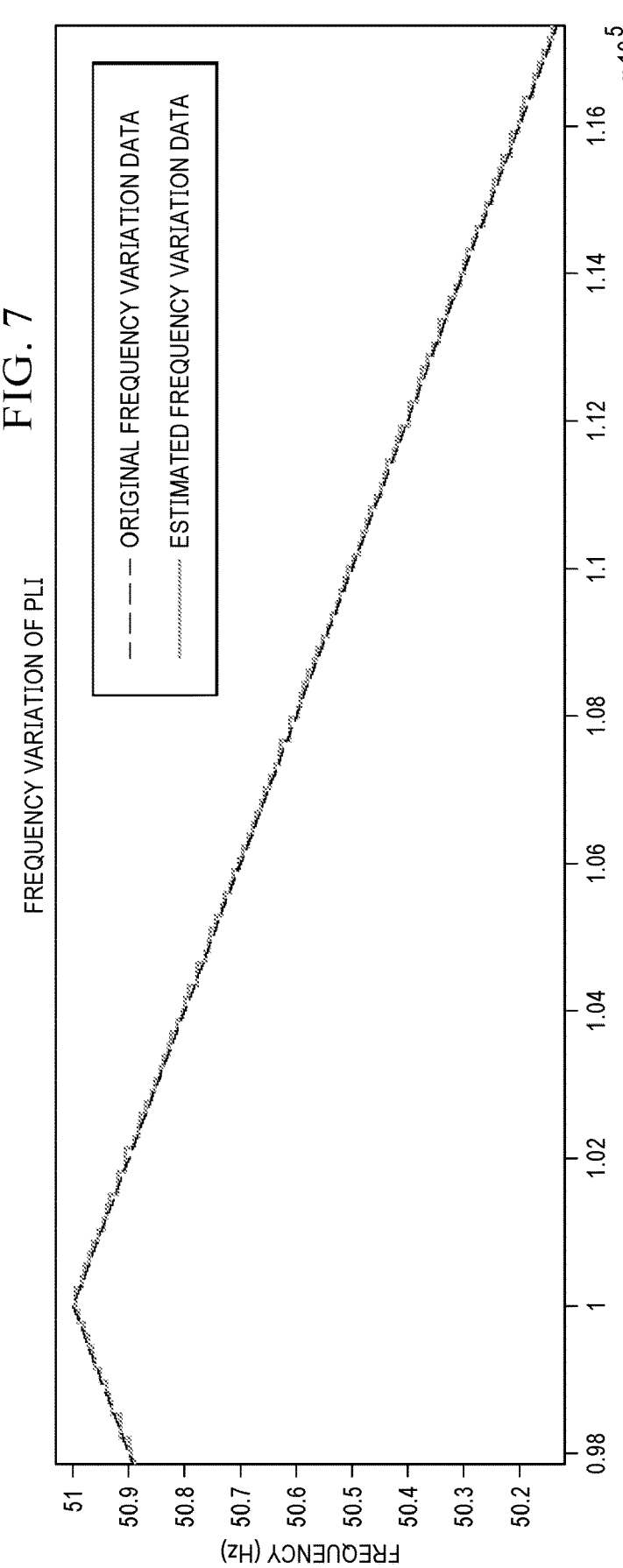
FIG. 7 is a graph showing an example of frequency tracking performance of the frequency tracking circuit of FIG. 6.

FIG. 7 is a graph showing an example of frequency tracking performance of the frequency tracking circuit 408. In FIG. 7, the y-axis is frequency, and the x-axis is sample count. In the example of FIG. 7, the frequency tracking circuit 408 accurately tracks frequency variation in a range of about 50.1 Hz to about 51 Hz. Examples of the frequency tracking circuit may track frequency in a range of 49-51 Hz or 59-61 Hz.

Figure 8:
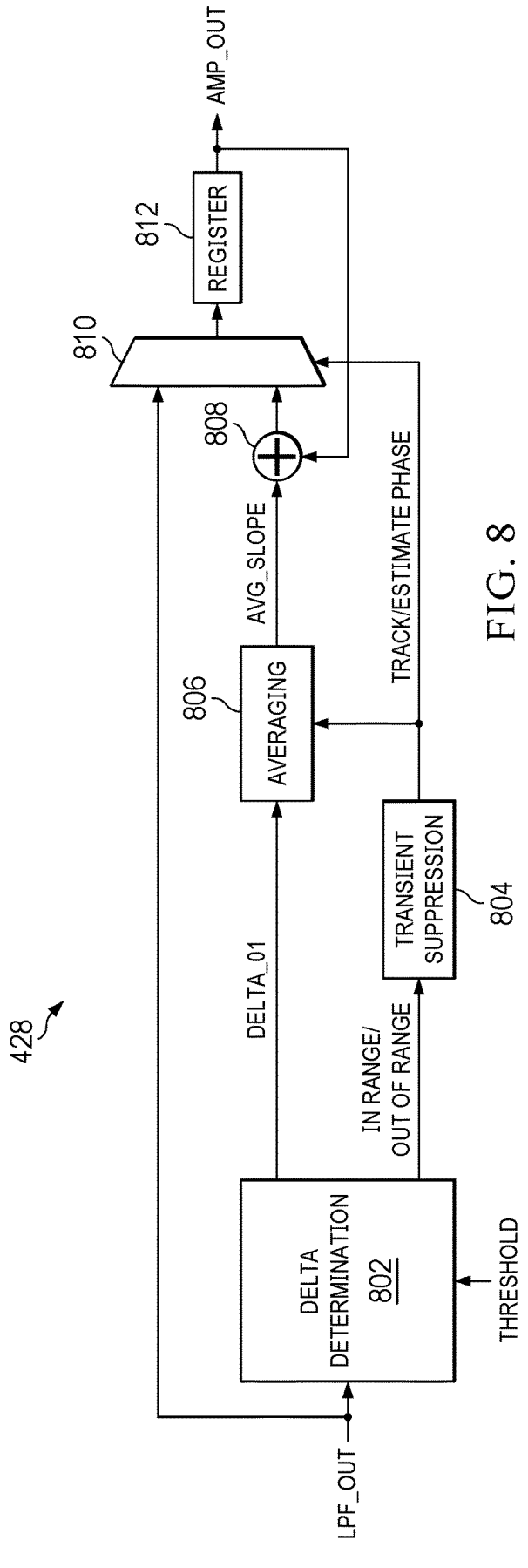
FIG. 8 is a block diagram of an example amplitude tracking circuit suitable for use in the power line interference suppression circuit of FIG. 4.

FIG. 8 is a block diagram of an example amplitude tracking circuit 428. The amplitude tracking circuit 428 includes a delta determination circuit 802, a transient suppression circuit 804, an averaging circuit 806, a summation circuit 808, a selector circuit 810, and a register 812. An input of the delta determination circuit 802 is coupled to the output of the low-pass filter circuit 426. The delta determination circuit 802 compares sequential samples of the low-pass output signal (LPF_OUT) received from the low-pass filter circuit 426, and determines the difference (the delta) in amplitude between the samples (e.g., between adjacent intervals (e.g., two adjacent intervals) of the low-pass output signal). The delta determination circuit 802 has a difference output and provides a difference signal (DELTA_01) representing the difference in amplitude between samples. The delta determination circuit 802 has a transient detected output and provides a transient detected signal (IN RANGE/ OUT OF RANGE) that indicates whether the difference in amplitude between samples of the low-pass output signal exceeds a difference threshold. The transient detected signal has a first state (e.g., a first logic level "0") indicating that the difference in amplitude exceeds the difference threshold, and a second state (e.g., a second logic level "1") indicating that the difference in amplitude does not exceed the difference threshold. The difference threshold may be provided by a controller or other circuit coupled to the delta determination circuit 802.

The transient detected output of the delta determination circuit 802 is coupled to an input of the transient suppression circuit 804. The transient suppression circuit 804 generates a track signal. The track signal has a first state (e.g., a first logic level "1") indicating that an amplitude signal (AMP_OUT) provided by the amplitude tracking circuit 428 is to track the amplitude of the low-pass output signal, and a second state (e.g., a second logic level "0") indicating that the amplitude signal is to be an estimate of the amplitude of the PLI based on previously determined amplitude values. The transient suppression circuit 804 sets the track signal to the second state responsive to the transient detected signal indicating that the difference in amplitude between samples of the low-pass output signal exceeds the difference threshold. If the track signal indicates that the difference threshold is exceeded, the transient suppression circuit 804 sets the track signal to the second state for a predetermined time (e.g., a selected number of samples (16 samples in some implementations)). The predetermined time is selected to exclude transient amplitude changes from the PLI amplitude determination.

The averaging circuit 806 has a first input coupled to the difference output of the delta determination circuit 802, and a second input coupled to the output of the transient suppression circuit 804. The averaging circuit 806 averages difference values received from the delta determination circuit 802 responsive to the track signal having the first state. Averaging is one example of filtering that the averaging circuit 806 can apply to the difference values to improve the accuracy of the amplitude estimation. Some examples of the averaging circuit 806 may apply different filtering, e.g., different low pass filtering. Accordingly, the averaging circuit 806 may also be referred to as a filtering circuit. Responsive to the track signal having the second state, the averaging circuit 806 excludes difference values received from the delta determination circuit 802 from the average. That is, while the track signal has the second state, DELTA_01 is excluded from the average to exclude transients from the average. An output signal (AVG_SLOPE) provided by the averaging circuit 806 represents an average slope of amplitude of the low-pass filter output signal.

The summation circuit 808 has a first input coupled to the output of the averaging circuit 806. The selector circuit 810 has a first input coupled to output of the low-pass filter circuit 426 for receipt of the low-pass output signal. The output of the summation circuit 808 is coupled to a second input of the selector circuit 810. A control input of the selector circuit 810 is coupled to the output of the transient suppression circuit 804. The selector circuit 810 passes the low-pass filter output signal responsive to the track signal having the first state, and passes the output signal provided by the summation circuit 808 responsive to the track signal having the second state. Accordingly, if no transient is present in the low-pass filter output signal, the selector circuit 810 passes the low-pass filter output signal as the amplitude of the PLI. If a transient is present in the low-pass filter output signal, the selector circuit 810 passes the estimated amplitude of the PLI provided by the summation circuit 808.

The output of the selector circuit 810 is coupled to an input of the register 812. The register 812 is a storage device that stores the amplitude value provided by the selector circuit 810. The output of the register 812 is coupled to a second input of the summation circuit 808, and to the second input of the multiplier 430.

Figure 9:
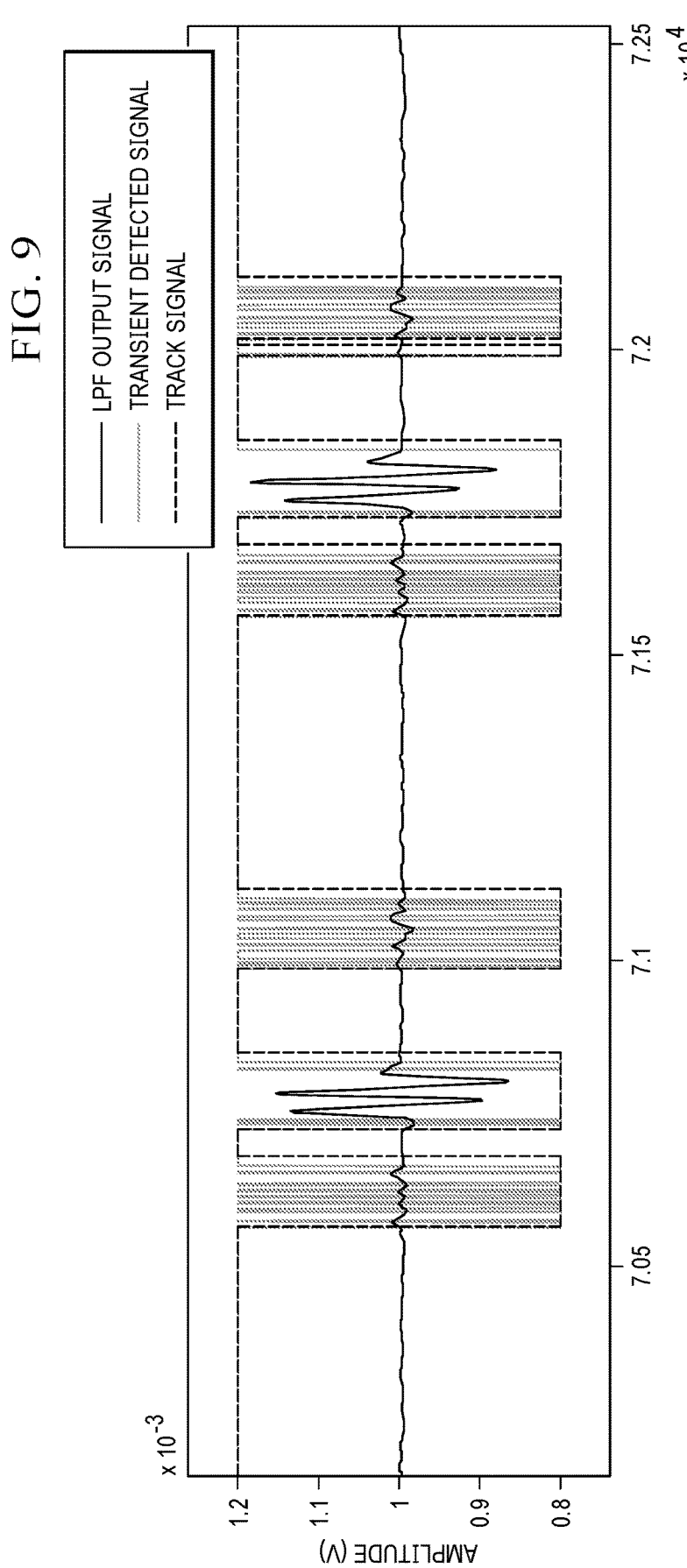
FIGS. 9 and 10 are graphs showing examples of transient suppression using the amplitude tracking circuit of FIG. 8.

FIG. 9 shows an example of signals in the amplitude tracking circuit 428. In FIG. 9, the y-axis is amplitude, and the x-axis is sample count. In FIG. 9, the low-pass filter output signal includes various transients which may be waves of the ECG signal. The delta determination circuit 802 detects the transients and sets the transient detected signal (to logic 0 (0.8 volts) in FIG. 9) responsive to detection of the transients. The transient suppression circuit 804 sets the track signal to the second state (e.g., logic 0 (0.8 volts)) responsive to the transient detected signal having a logic 0 state. Accordingly, the amplitude tracking circuit 428 provides the low-pass output signal as the amplitude value if the track signal is in the first state, and includes the low-pass output signal in the average if the track signal is in the first state. If the track signal is in the second state, the amplitude tracking circuit 428 excludes low-pass output signal from the average, and provides an amplitude value based on the previously determined average value.

Figure 10:
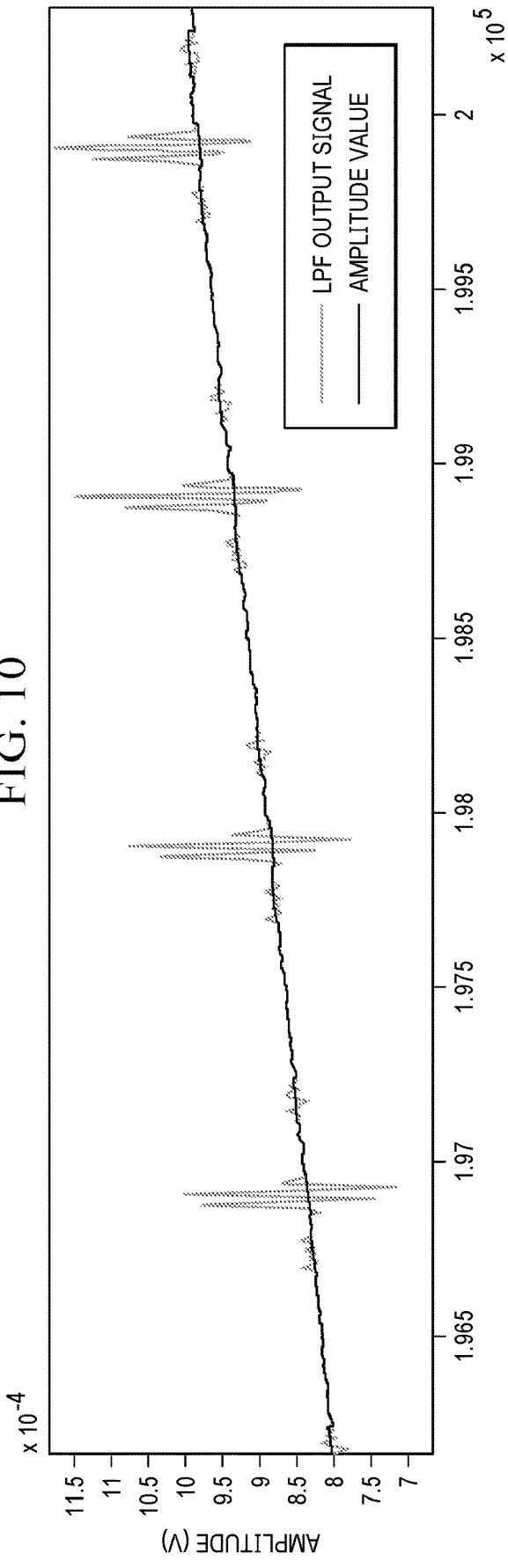

FIG. 10 is a graph showing low-pass filter output signal and the amplitude values provided by the amplitude tracking circuit 428 based on the low-pass filter output signal. In FIG. 10, the y-axis is amplitude, and the x-axis is sample count. The low-pass filter circuit 426 excludes transient data from amplitude value determination. Accordingly, the amplitude values provided by the low-pass filter circuit 426 are relatively smooth, while the low-pass filter output signal includes transients.

Figure 11:
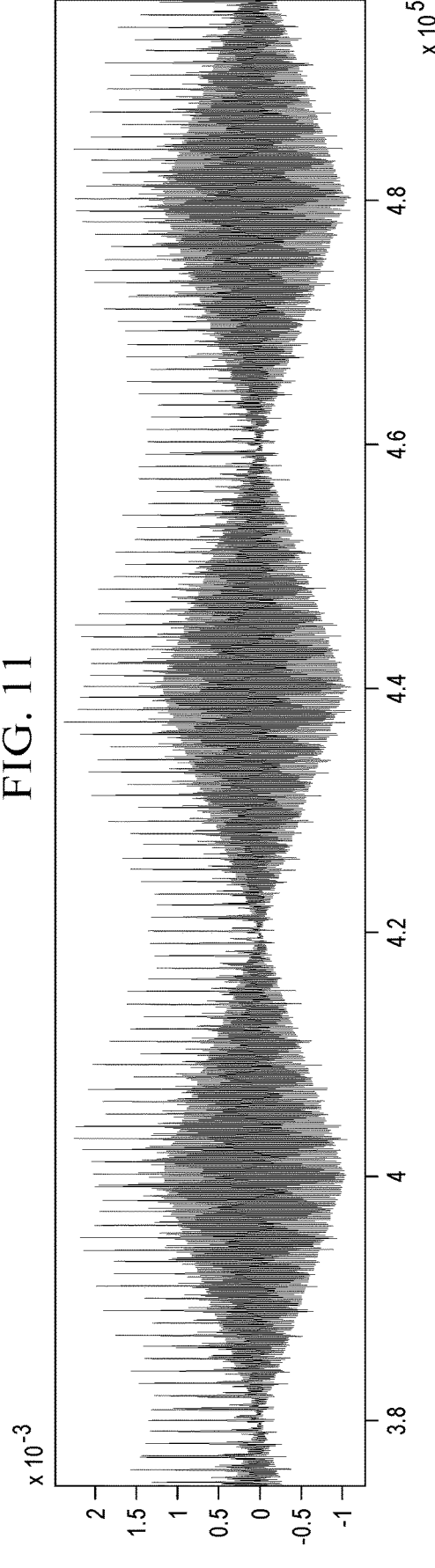
FIG. 11 is a graph of an example ECG signal with power line interference that varies in frequency and amplitude.

FIG. 11 is a graph of an example ECG signal with power line interference that varies in frequency and amplitude. In FIG. 11, the y-axis is amplitude, and the x-axis is sample count. The ECG signal is about 1.5 mV in amplitude. The PLI signal varies in amplitude at about 50 microvolts/s, and varies in frequency at about 0.05 Hz/s with 50 Hz, 100 Hz, and 150 Hz frequencies.

Figure 12:
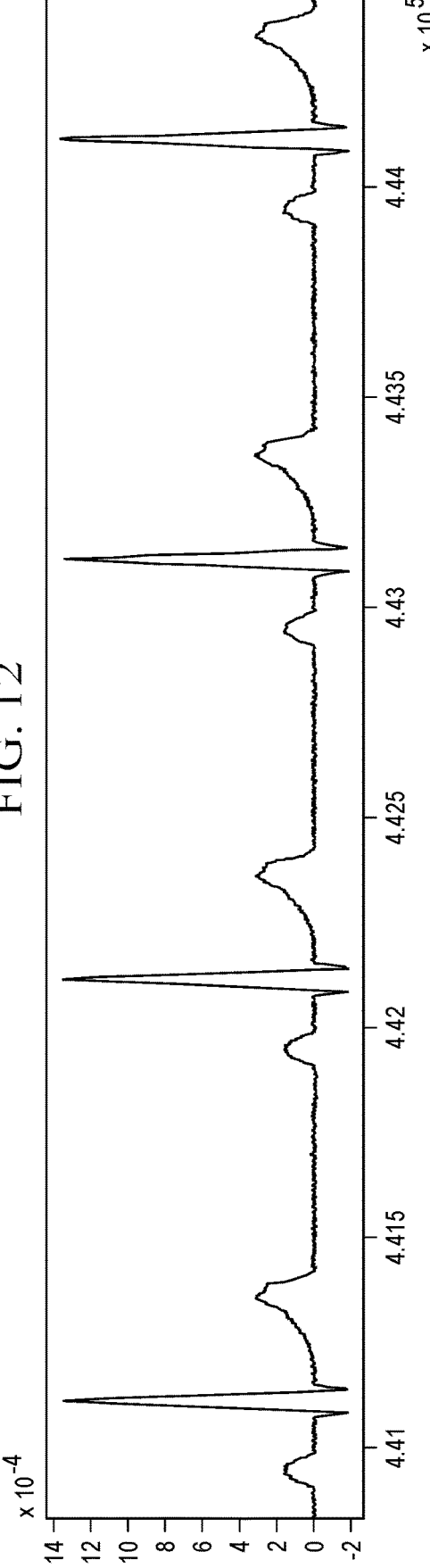
FIG. 12 is a graph of the ECG signal of FIG. 11 after processing by the power line interference suppression circuit of FIG. 4.

FIG. 12 is a graph of the amplified ECG signal of FIG. 11 after processing by the PLI suppression circuit 104. In FIG. 12, the y-axis is amplitude, and the x-axis is sample count. FIG. 12 shows that the PLI suppression circuit 104 suppresses the frequency and amplitude variant PLI without introducing undesirable artifacts, such as ringing.

Figure 13:
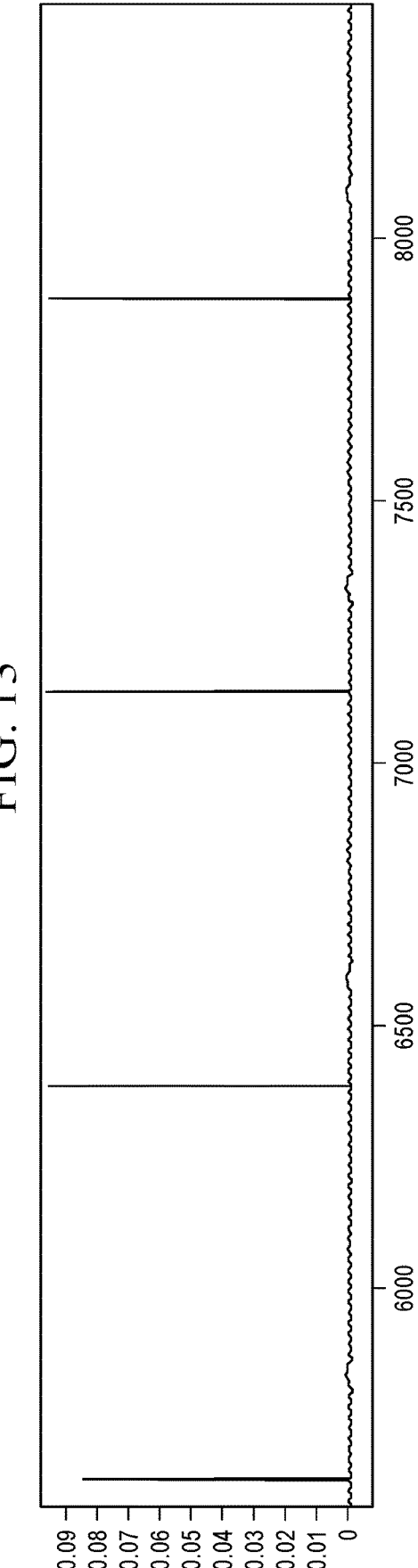
FIG. 13 is a graph of an ECG signal that includes pacemaker pulses and power line interference.

FIG. 13 is a graph of an ECG signal that includes pacemaker pulses and PLI. In FIG. 13, the y-axis is amplitude, and the x-axis is sample count. The ECG signal is about 1.5 mV in amplitude. The pacemaker pulses are about 100 mV in amplitude. PLI at about 50 Hz having about 0.5 mV amplitude is present on the ECG signal.

Figure 14:
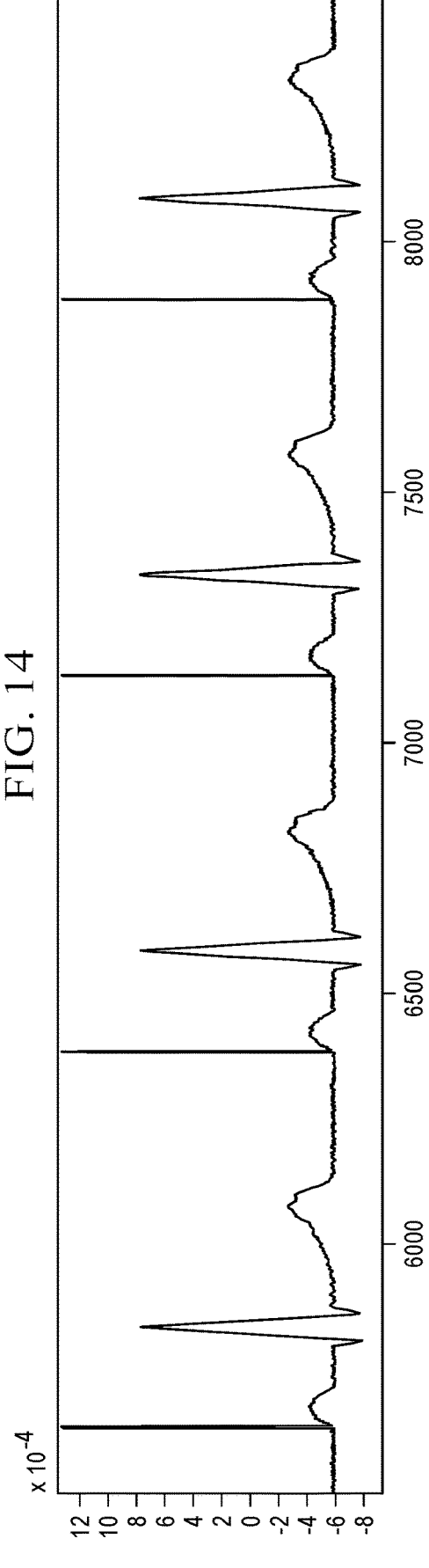
FIG. 14 is a graph of the amplified ECG signal of FIG. 13 after processing by the power line interference suppression circuit of FIG. 4.

FIG. 14 is a graph of the amplified ECG signal of FIG. 13 after processing by the PLI suppression circuit 104. In FIG. 14, the y-axis is amplitude, and the x-axis is sample count. FIG. 14 shows that after PLI suppression, the ECG signal and the pacemaker pulses remain, while the PLI suppression circuit 104 has suppressed the PLI without introducing undesirable artifacts.

The circuits described herein, including the frequency tracking circuit 408, and the PLI synthesizer circuits 410, 414, and 416, may be implemented as dedicated hardware circuits (e.g., on an integrated circuit) that provide the functionality described herein. In some examples, all, or a portion, of the frequency tracking circuit 408, or the PLI synthesizer circuits 410, 414, and 416 may be implemented using a processor (e.g., a digital signal processor, a general-purpose microprocessor, etc.) that executes instructions stored in a non-transitory computer-readable medium (e.g., a memory) to provide the functionality described herein.

In this description, the term "couple" may cover connections, communications, or signal paths that enable a functional relationship consistent with this description. For example, if device A generates a signal to control device B to perform an action: (a) in a first example, device A is coupled to device B by direct connection; or (b) in a second example, device A is coupled to device B through intervening component C if intervening component C does not alter the functional relationship between device A and device B, such that device B is controlled by device A via the control signal generated by device A.

As used herein, the terms "terminal," "node," "interconnection," "pin" and "lead" are used interchangeably. Unless specifically stated to the contrary, these terms are generally used to mean an interconnection between or a terminus of a device element, a circuit element, an integrated circuit, a device or other electronics or semiconductor component.

A circuit or device that is described herein as including certain components may instead be adapted to be coupled to those components to form the described circuitry or device. For example, a structure described as including one or more semiconductor elements (such as transistors), one or more passive elements (such as resistors, capacitors, and/or inductors), and/or one or more sources (such as voltage and/or current sources) may instead include only the semiconductor elements within a single physical device (e.g., a semiconductor die and/or integrated circuit (IC) package) and may be adapted to be coupled to at least some of the passive elements and/or the sources to form the described structure either at a time of manufacture or after a time of manufacture, for example, by an end-user and/or a third-party.

Circuits described herein are reconfigurable to include additional or different components to provide functionality at least partially similar to functionality available prior to the component replacement. Components shown as resistors, unless otherwise stated, are generally representative of any one or more elements coupled in series and/or parallel to provide an amount of impedance represented by the resistor shown. For example, a resistor or capacitor shown and described herein as a single component may instead be multiple resistors or capacitors, respectively, coupled in parallel between the same nodes. For example, a resistor or capacitor shown and described herein as a single component may instead be multiple resistors or capacitors, respectively, coupled in series between the same two nodes as the single resistor or capacitor.

While certain elements of the described examples are included in an integrated circuit and other elements are external to the integrated circuit, in other example embodiments, additional or fewer features may be incorporated into the integrated circuit. In addition, some or all of the features illustrated as being external to the integrated circuit may be included in the integrated circuit and/or some features illustrated as being internal to the integrated circuit may be incorporated outside of the integrated. As used herein, the term "integrated circuit" means one or more circuits that are: (i) incorporated in/over a semiconductor substrate; (ii) incorporated in a single semiconductor package; (iii) incorporated into the same module; and/or (iv) incorporated in/on the same printed circuit board.

In this description, unless otherwise stated, "about," "approximately" or "substantially" preceding a parameter means being within +/−10 percent of that parameter or, if the parameter is zero, a reasonable range of values around zero.

Modifications are possible in the described embodiments, and other embodiments are possible, within the scope of the claims.

What is claimed is:
1. A circuit comprising:
an interference frequency tracking circuit including:
an analog-to-digital converter (ADC) having an output and configured to digitize an interference signal extracted from a target signal;
a bandpass filter circuit having an input coupled to the output of the ADC, and an output, the bandpass filter circuit configured to pass a frequency range of the interference signal;
a cyclic event detector having an input coupled to the output of the bandpass filter circuit, and an output, the cyclic event detector configured to identify a cyclic event of the interference signal;
an averaging circuit having an input coupled to the output of the cyclic event detector, and an output, the averaging circuit configured to provide an average time value representing an average time between cyclic events detected by the cyclic event detector; and
a frequency selection circuit having an input coupled to the output of the averaging circuit, and an output, the frequency selection circuit configured to provide a frequency selection value representing a frequency of the interference signal based on the average time;
a power line interference (PLI) synthesizer circuit having an input coupled to the output of the frequency selection circuit, and an output, the PLI synthesizer circuit configured to generate a correction signal based on the frequency selection value; and a summing circuit having an input coupled to the output of the PLI synthesizer circuit, the summing circuit configured to subtract the correction signal from the target signal.
2. The circuit of claim 1, wherein the cyclic event detector is configured to identify a peak of the interference signal or identify a zero-crossing of the interference signal.
3. The circuit of claim 1, wherein the interference signal is provided in a right leg drive signal, and the target signal is an electrocardiogram signal.
4. The circuit of claim 1, wherein:
the summing circuit is a first summing circuit; and
the PLI synthesizer circuit includes:
a PLI sine estimation circuit having an output;
a PLI cosine estimation circuit having an output; and
a second summing circuit having a first input coupled to the output of the PLI sine estimation circuit, a second input coupled to the output of PLI cosine estimation circuit, and an output coupled to the input of the first summing circuit, the second summing circuit configured to sum output signals of the PLI sine estimation circuit and the PLI cosine estimation circuit.
5. The circuit of claim 4, wherein the PLI sine estimation circuit includes:
a sine generator circuit having an output, the sine generator circuit configured to provide a sine signal based on the frequency selection value;
a first multiplier having an input coupled to the output of the sine generator circuit, and an output, the first multiplier configured to multiply the target signal and the sine signal;
a low-pass filter circuit having an input coupled to the output of the first multiplier, and an output;
an amplitude tracking circuit having an input coupled to the output of the low-pass filter circuit, and an output; and
a second multiplier having a first input coupled to the output of the amplitude tracking circuit and a second input coupled to the output of the sine generator circuit, and an output coupled to a first input of the second summing circuit.
6. The circuit of claim 5, wherein:
the low-pass filter circuit is a first low-pass filter circuit, and the amplitude tracking circuit is a first amplitude tracking circuit; and
the PLI cosine estimation circuit includes:
a cosine generator circuit having an output, the cosine generator circuit configured to provide a cosine signal based on the frequency selection value;
a third multiplier having an input coupled to the output of the cosine generator circuit, and an output, the third multiplier configured to multiply the target signal and the cosine signal;
a second low-pass filter circuit having an input coupled to the output of the third multiplier, and an output;
a second amplitude tracking circuit having an input coupled to the output of the second low-pass filter circuit, and an output; and
a fourth multiplier having a first input coupled to the output of the second amplitude tracking circuit and a second input coupled to the output of the cosine generator circuit, and an output coupled to the second input of the second summing circuit.
7. The circuit of claim 5, wherein the amplitude tracking circuit is configured to:

detect transients on a low-pass output signal received from the low-pass filter circuit;

provide an amplitude signal that tracks an amplitude of the low-pass output signal responsive to no transient being detected on the low-pass output signal; and provide the amplitude signal as an estimate based on a slope of the low-pass output signal during an interval prior to a detected transient responsive to a transient being detected.

8. The circuit of claim 5, wherein the amplitude tracking circuit includes:

a delta determination circuit having an input coupled to the output of the low-pass filter circuit, a first output, and a second output, the delta determination circuit configured to:

provide a difference signal indicating a difference in amplitude between two adjacent intervals of signal received from the low-pass filter circuit; and provide a transient detected signal indicating whether the difference exceeds a difference threshold;

a transient suppression circuit having an input coupled to the first output of the delta determination circuit, and an output, the transient suppression circuit configured to provide a track signal having a first state indicating that an amplitude signal provided by the amplitude tracking circuit is to track the amplitude of the signal received from the low-pass filter circuit, and a second state indicating that the amplitude signal is to be an estimate of the amplitude of the interference signal;

an averaging circuit having a first input coupled to the second output of the delta determination circuit, a second input coupled to the output of the transient suppression circuit, and an output, the averaging circuit configured to:

average the difference signal responsive to the track signal having the first state; and not average the difference signal responsive to the track signal having the second state;

a summation circuit having a first input coupled to the output of the averaging circuit, a second input, and an output; and a selector circuit having a first input coupled to the output of the low-pass filter circuit, a second input coupled to the output of the summation circuit, a control input coupled to the output of the transient suppression circuit, and an output coupled to second input of the summation circuit.

9. The circuit of claim 1, wherein:

the PLI synthesizer circuit is a first PLI synthesizer circuit;

the summing circuit is a first summing circuit; and the circuit includes:

a second PLI synthesizer circuit having an input coupled to the output of the frequency selection circuit, and an output, the second PLI synthesizer circuit configured to generate a correction signal that is a harmonic of a frequency represented by the frequency selection value; and a second summing circuit having a first input coupled to the output of the first PLI synthesizer circuit, a second input coupled to the output of the second PLI synthesizer circuit, and an output coupled to the input of the first summing circuit.

10. A circuit comprising:

an interference frequency tracking circuit having an output, the interference frequency tracking circuit configured to track a frequency of an interference signal derived from a target signal, and provide a frequency selection value representing the frequency of the interference signal;

a power line interference (PLI) synthesizer circuit having an input coupled to the output of the interference frequency tracking circuit, and an output, the PLI synthesizer circuit configured to:

generate, based on the frequency selection value, a correction signal at the frequency of the interference signal;

adjust a phase of the correction signal to match a phase of the interference signal in the target signal; and adjust an amplitude of the correction signal to match an amplitude of the interference signal in the target signal; and a summing circuit having a first input coupled to the output of the PLI synthesizer circuit, the summing circuit configured to subtract the correction signal from the target signal.

11. The circuit of claim 10, wherein:

the summing circuit is a first summing circuit; and the PLI synthesizer circuit includes:

a PLI sine estimation circuit having an output, a PLI cosine estimation circuit having an output, and a second summing circuit having a first input coupled to the output of the PLI sine estimation circuit, and a second input coupled to the output of the PLI cosine estimation circuit, the second summing circuit configured to provide the correction signal by summing output signals of the PLI sine estimation circuit and the PLI cosine estimation circuit, the PLI sine estimation circuit including:

a sine generator circuit having an output, the sine generator circuit configured to provide a sine signal based on the frequency selection value;

a first multiplier having an input coupled to the output of the sine generator circuit, and an output, the first multiplier configured to multiply the target signal and the sine signal;

a low-pass filter circuit having an input coupled to the output of the first multiplier, and an output;

an amplitude tracking circuit having an input coupled to the output of the low-pass filter circuit, and an output; and a third multiplier having a first input coupled to the output of the amplitude tracking circuit and a second input coupled to the output of the sine generator circuit, and an output coupled to the first input of the second summing circuit.

12. The circuit of claim 11, wherein:

the low-pass filter circuit is a first low-pass filter circuit, and the amplitude tracking circuit is a first amplitude tracking circuit; and the PLI cosine estimation circuit includes:

a cosine generator circuit having an output, the cosine generator circuit configured to provide a cosine signal based on the frequency selection value;

a third multiplier having an input coupled to the output of the cosine generator circuit, and an output, the third multiplier configured to multiply the target signal and the cosine signal;

a second low-pass filter circuit having an input coupled to the output of the third multiplier, and an output;

a second amplitude tracking circuit having an input coupled to the output of the second low-pass filter circuit, and an output; and a fourth multiplier having a first input coupled to the output of the second amplitude tracking circuit and a second input coupled to the output of the cosine generator circuit, and an output coupled to the second input of the second summing circuit.

13. The circuit of claim 11, wherein the amplitude tracking circuit is configured to:

detect transients on a low-pass output signal received from the low-pass filter circuit;

provide an amplitude signal that tracks an amplitude of the low-pass output signal responsive to no transient being detected on the low-pass output signal; and provide the amplitude signal as an estimate based on a slope of the low-pass output signal during an interval prior to a detected transient responsive to a transient being detected.

14. The circuit of claim 11, wherein the amplitude tracking circuit includes:

a delta determination circuit having an input coupled to the output of the low-pass filter circuit, a first output, and a second output, the delta determination circuit configured to:

provide a difference signal indicating a difference in amplitude between two adjacent intervals of signal received from the low-pass filter circuit; and provide a transient detected signal indicating whether the difference exceeds a difference threshold;

a transient suppression circuit having an input coupled to the first output of the delta determination circuit, and an output, the transient suppression circuit configured to provide a track signal having a first state indicating that an amplitude signal provided by the amplitude tracking circuit is to track the amplitude of the signal received from the low-pass filter circuit, and a second state indicating that the amplitude signal is to be an estimate of the amplitude of the interference signal;

an averaging circuit having a first input coupled to the second output of the delta determination circuit a second input coupled to the output of the transient suppression circuit, and an output, the averaging circuit configured to:

average the difference signal responsive to the track signal having the first state; and not average the difference signal responsive to the track signal having the second state;

a summation circuit having a first input coupled to the output of the averaging circuit, a second input, and an output; and a selector circuit having a first input coupled to the output of the low-pass filter circuit, a second input coupled to the output of the summation circuit, a control input coupled to the output of the transient suppression circuit, and an output coupled to the second input of the summation circuit.

15. The circuit of claim 10, wherein:

the PLI synthesizer circuit is a first PLI synthesizer circuit;

the summing circuit is a first summing circuit; and the circuit includes:

a second PLI synthesizer circuit having an input coupled to the output of the interference frequency tracking circuit, and an output, the second PLI synthesizer circuit configured to generate a correction signal that is a harmonic of a frequency represented by the frequency selection value; and a second summing circuit having a first input coupled to the output of the first PLI synthesizer circuit, a second input coupled to the output of the second PLI synthesizer circuit, and an output coupled to the input of the first summing circuit.

16. The circuit of claim 10, wherein the interference frequency tracking circuit includes an analog-to-digital converter (ADC) has an output, the ADC configured to digitize the interference signal;

a bandpass filter circuit having an input coupled to the output of the ADC, and an output, the bandpass filter circuit configured to pass frequency range of the interference signal;

a cyclic event detector having an input coupled to the output of the bandpass filter circuit, and an output, the cyclic event detector configured to identify a cyclic event of the interference signal;

an averaging circuit having an input coupled to the output of the cyclic event detector, and an output, the averaging circuit configured to provide an average time value representing an average time between events detected by the cyclic event detector; and a frequency selection circuit having an input coupled to the output of the averaging circuit, the frequency selection circuit configured to provide the frequency selection value based on the average time.

17. The circuit of claim 16, wherein the cyclic event detector is configured to identify a peak of the interference signal or identify a zero-crossing of the interference signal.

18. An electrocardiogram (ECG) system comprising:

an interference suppression circuit having an ECG signal input, a right leg drive (RLD) signal input coupled to an RLD terminal providing an RLD signal, and an ECG signal output, the interference suppression circuit including:

an interference frequency tracking circuit having an RLD input coupled to the RLD signal input, and a frequency output, the interference frequency tracking circuit configured to track a frequency of a power line interference (PLI) signal present in the RLD signal, and provide, at the frequency output, a frequency selection value representing the frequency of the PLI signal; and a PLI synthesizer circuit having an input coupled to the frequency output of the interference frequency tracking circuit, and a synthesizer output, the PLI synthesizer circuit configured to provide a correction signal based on the frequency selection value; and a summing circuit having a first input coupled to the synthesizer output of the PLI synthesizer circuit, a second input coupled to the ECG signal input, the summing circuit configured to subtract the correction signal from the ECG signal.

19. The ECG system of claim 18, wherein the interference frequency tracking circuit includes:

an analog-to-digital converter (ADC) having an input coupled to the RLD terminal, and an output, the ADC configured to digitize the RLD signal;

a bandpass filter circuit having an input coupled to the output of the ADC, and an output, the bandpass filter circuit configured to pass a frequency range of the PLI signal;

a cyclic event detector having an input coupled to the output of the bandpass filter circuit, and an output, the cyclic event detector configured to identify a cyclic event of the PLI signal;

an averaging circuit having an input coupled to the output of the cyclic event detector, and an output, the averaging circuit configured to provide an average time value representing an average time between events detected by the cyclic event detector; and a frequency selection circuit having an input coupled to the output of the averaging circuit, the frequency selection circuit configured to provide the frequency selection value based on the average time value.

20. The ECG system of claim 19, wherein:

the summing circuit is a first summing circuit; and the PLI synthesizer circuit includes:

a PLI sine estimation circuit having an output, a PLI cosine estimation circuit having an output, and a second summing circuit having a first input coupled to the output of the PLI sine estimation circuit, a second input coupled to the output of PLI cosine estimation circuit, and an output coupled to the first input of the first summing circuit, the second summing circuit configured to sum output signals of the PLI sine estimation circuit and the PLI cosine estimation circuit;

the PLI sine estimation circuit includes:

a sine generator circuit having an output, the sine generator circuit configured to provide a sine signal based on the frequency selection value;

a first multiplier having an input coupled to the output of the sine generator circuit, and an output, the first multiplier configured to multiply the ECG signal and the sine signal;

a low-pass filter circuit having an input coupled to the output of the first multiplier, and an output;

an amplitude tracking circuit having an input coupled to the output of the low-pass filter circuit, and an output; and a second multiplier having a first input coupled to the output of the amplitude tracking circuit and a second input coupled to the output of the sine generator circuit, and an output coupled to a first input of the second summing circuit.

* * * * *